(12) United States Patent
Chen et al.

(10) Patent No.: US 6,303,633 B1
(45) Date of Patent: Oct. 16, 2001

(54) HETEROARYL AMINES AS NOVEL ACETYLCHOLINESTERASE INHIBITORS

(75) Inventors: Yuhpyng L. Chen, Waterford; Arthur A. Nagel, Gales Ferry, both of CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/438,712

(22) Filed: Nov. 11, 1999

Related U.S. Application Data

(62) Division of application No. 08/957,639, filed on Oct. 24, 1997, now Pat. No. 6,124,321, which is a division of application No. 08/689,745, filed on Aug. 13, 1996, now Pat. No. 5,965,574, which is a division of application No. 08/211,044, filed as application No. PCT/US92/07230 on Aug. 31, 1992, now Pat. No. 5,574,046, which is a continuation of application No. 07/771,283, filed on Oct. 3, 1991, now abandoned.

(51) Int. Cl.$^7$ ............ A61K 31/445; C07D 401/06; C07D 409/06
(52) U.S. Cl. .......... 514/323; 514/324; 546/201; 546/202
(58) Field of Search ............ 546/201, 202; 514/323, 324

(56) References Cited

U.S. PATENT DOCUMENTS

| | | | |
|---|---|---|---|
| 2,814,625 | 11/1957 | Speeter et al. | 546/492 |
| 4,064,255 | * 12/1977 | Champseix et al. | 514/323 |
| 4,167,632 | 9/1979 | Jaunin | 544/143 |
| 4,791,104 | 12/1988 | Picciola et al. | 514/58 |
| 4,839,377 | 6/1989 | Bays et al. | 514/415 |
| 4,971,980 | 11/1990 | Giani et al. | 514/322 |
| 5,273,974 | * 12/1993 | Goto et al. | 514/221 |

FOREIGN PATENT DOCUMENTS

| | | |
|---|---|---|
| 0288563 | 11/1988 | (EP) . |
| 0296560 | 12/1988 | (EP) . |
| 0351282 | 1/1990 | (EP) . |
| 0378207 | 7/1990 | (EP) . |
| 0441517 | 11/1991 | (EP) . |
| 0449186 | 11/1991 | (EP) . |
| 0487071 | 5/1992 | (EP) . |
| 562832 | * 9/1993 | (EP) . |

OTHER PUBLICATIONS

Djuric et al., "Chemoselective Reductions of 2–Acyl–1H–indole–3–carboxaldehydes", *J. Heterocyclic Chem.*, 22, 1425 (1985).
Williams et al. "Toxicity and enzyme activity . . . " CA 68:38517, 1967.*

\* cited by examiner

*Primary Examiner*—Ceila Chang
(74) *Attorney, Agent, or Firm*—Peter C. Richardson; Paul H. Ginsburg; Seth H. Jacobs

(57) ABSTRACT

Compounds of the formula

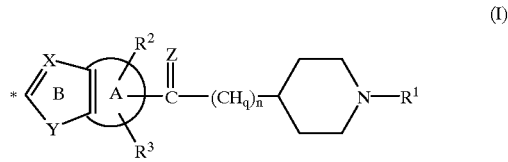

(I)

wherein ring A, ring B, ring D, $R^2$, $R^3$, $R^4$, $R^5$, $R^6$, $R^{11}$, $R^{12}$, $R^{13}$, E, G, X and P are as defined below. The compounds of formula I are cholinesterase inhibitors and are useful in enhancing memory in patients suffering from dementia and Alzheimer's disease.

17 Claims, No Drawings

HETEROARYL AMINES AS NOVEL ACETYLCHOLINESTERASE INHIBITORS

This application is a divisional application of Ser. No. 08/957,639, filed Oct. 24, 1997, now U.S. Pat. No. 6,124, 321, which is a divisional application of Ser. No. 08/689, 745, filed Aug. 13, 1996 now U.S. Pat. No. 5,963,574, which is a divisional application of Ser. No. 08/211,044, filed Mar. 9, 1994, now U.S. Pat. No. 5,574,046, which was a 35 U.S.C. §371 filing of PCT application PCT/US92/07230, filed Aug. 31, 1992, which is a continuation of Ser. No. 07/771,283, filed Oct. 3, 1991 abandoned.

BACKGROUND OF THE INVENTION

The present invention relates to heteroaryl amines of the formula I below, and pharmaceutically acceptable salts of such compounds. The compounds of formula I are acetylcholinesterase inhibitors and are useful in enhancing memory in patients suffering from dementia and Alzheimer's disease.

Alzheimer's disease is associated with degeneration of cholinergic neurons in the basal forebrain that play a fundamental role in cognitive functions, including memory. Becker et al., Drug Development Research, 12, 163–195 (1988). As a result of such degeneration, patients suffering from the disease exhibit a marked reduction in acetylcholine synthesis, choline acetyltransferase activity, acetylcholinesterase activity and choline uptake.

It is known that acetylcholinesterase inhibitors are effective in enhancing cholinergic activity and useful in improving the memory of Alzheimer's patients. By inhibiting acetylcholinesterase enzyme, these compounds increase the level of the neurotransmitter acetylcholine, in the brain and thus enhance memory. Becker et al., supra, report that behavioral changes following cholinesterase inhibition appear to coincide with predicted peak levels of acetylcholine in the brain. They also discuss the efficacy of the three known acetylcholinesterase inhibitors physostigmine, metrifonate, and tetrahydroaminoacridine.

U.S. patent application Ser. No. 07/639,614, filed Jan. 10, 1991, and U.S. patent application Ser. No. 07/676,918, filed Mar. 28, 1991, both of which are assigned in common with the present application, also refer to heteroaryl amine acetylcholinesterase inhibitors.

SUMMARY OF THE INVENTION

The present invention relates to compounds of the formula

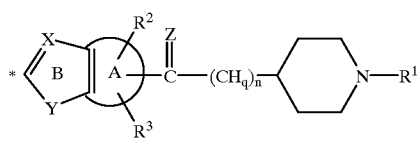

(I)

wherein one of $R^2$, $R^3$ and the side chain containing

may optionally be attached to the carbon atom designated by an asterisk in ring B rather than to a member of ring A;

ring A is benzo, thieno, pyrido, pyrazino, pyrimido, furano, seleno, pyrrolo, thiazolo, or imidazolo;

$R^1$ is phenyl, phenyl-$(C_1-C_6)$alkyl, cinnamyl or heteroarylmethyl, wherein the heteroaryl moiety of said heteroarylmethyl is selected from imidazolo, thiazolo, thieno, pyrido and isoxazolo, and wherein said phenyl and said heteroaryl moiety may optionally be substituted with one or two substituents independently selected from $(C_1-C_6)$alkyl, $(C_1-C_6)$alkoxy and halo;

$R^2$ and $R^3$ are independently selected from hydrogen, $(C_1-C_6)$alkoxy, $(C_1-C_6)$alkyl optionally substituted with from one to three fluorine atoms, benzyloxy, hydroxy, phenyl, benzyl, halo, nitro, cyano, $COOR^4$, $CONHR^4$, $NR^4R^5$, $NR^4COR^5$, or $SO_pCH_2$-phenyl wherein p is 0, 1 or 2;

or $R^2$ and $R^3$ are attached to adjacent carbon atoms and form, together with the carbons to which they are attached, a five or six membered ring wherein each atom of the ring is carbon, nitrogen or oxygen (e.g., a methylenedioxy, ethylenedioxy or lactam ring);

$R^4$ and $R^5$ are independently selected from hydrogen and $(C_1-C_6)$alkyl, or $R^4$ and $R^5$, when part of said $NR^4R^5$, optionally form, together with the nitrogen to which they are attached, a ring containing four to eight members wherein one atom of the ring is nitrogen and the others are carbon, oxygen or nitrogen, or $R^4$ and $R^5$, when part of said $NR^4COR^5$, optionally form, together with the nitrogen and carbon to which they are attached, a four to eight membered lactam ring;

X is nitrogen or CH;

Y is oxygen, sulfur or $NR^6$;

$R^6$ is hydrogen, $(C_1-C_6)$alkyl, $CO(C_1-C_6)$alkyl or $SO_2$—, phenyl, wherein the phenyl moiety of said $SO_2$-phenyl may optionally be substituted with from one to five substituents independently selected from $(C_1-C_4)$alkyl;

n is an integer from 1 to 4;

each q is independently 1 or 2; and

Z is oxygen or sulfur;

with the proviso that any $CH_q$ group wherein q is 1 must be attached to one and only one other $CH_q$ group wherein q is 1.

The present invention also relates to the pharmaceutically acceptable acid addition salts of compounds of the formula I. Examples of such pharmaceutically acceptable acid addition salts are the salts of hydrochloric acid, p-toluenesulfonic acid, fumaric acid, maleic acid, citric acid, succinic acid, salicylic acid, oxalic acid, hydrobromic acid, phosphoric acid, methanesulfonic acid, tartaric acid, di-p-toluoyl tartaric acid, and mandelic acid.

This invention further relates to a pharmaceutically composition for inhibiting acetylcholinesterase comprising a compound of the formula I or a pharmaceutically acceptable acid addition salt thereof, and a pharmaceutically acceptable carrier.

The invention further relates to a method for inhibiting acetylcholinesterase in a mammal comprising administering to a mammal an amount of a compound of the formula I or a pharmaceutically acceptable acid addition salt thereof effective in inhibiting acetylcholinesterase.

The invention further relates to a method for enhancing memory or treating or preventing Alzheimer's disease in a mammal comprising administering to a mammal an amount of a compound of the formula I or a pharmaceutically acceptable acid addition or salt thereof effective in enhancing memory or treating or preventing Alzheimer's disease.

The term "mammal", as used herein, includes humans.

The term "halo", as used herein, includes chloro, bromo or fluoro.

Preferred compounds of this invention are compounds of the formula

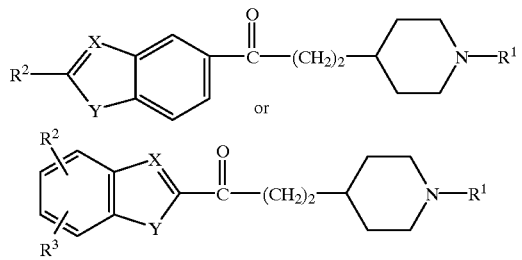

wherein X is CH, CCH$_3$, CCH$_2$CH$_3$ or N; Y is NH, NCH$_3$, NCH$_2$CH$_3$, S, O or NSO$_2$C$_6$H$_5$; R$^2$ and R$^3$ are independently selected from the group consisting of (C$_1$–C$_4$)alkyl, chloro, fluoro, methoxy, amino and

or R$^2$ and R$^3$, together with the carbons to which they are attached, form a γ-lactam ring; and R$^1$ is benzyl, methoxybenzyl, fluorobenzyl or a group of the formula

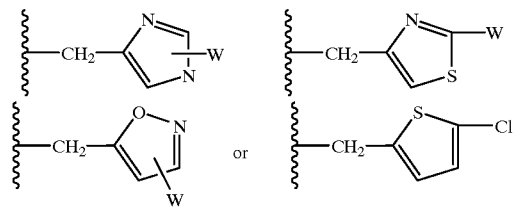

wherein W is hydrogen, (C$_1$–C$_6$)alkyl, phenyl or benzyl.

Specific preferred compounds of the invention are:
1-(2-methyl-1H-benzimidazol-5-yl)-3-[1-(phenylmethyl)-4-piperidinyl]-1-propanone;
1-(2-phenyl-1H-benzimidazol-5-yl)-3-[1-(phenylmethyl)-4-piperidinyl]-1-propanone;
1-(1-ethyl-2-methyl-1H-benzimidazol-5-yl)-3-[1-(phenylmethyl)-4-piperidinyl)-1-propanone;
1-(2-methyl-6-benzothiazolyl)-3-(1-(phenylmethyl)-4-piperidinyl]-1-propanone;
1-(2-methyl-6-benzothiazolyl)-3-[1-[(2-methyl-4-thiazolyl)methyl]-4-piperidinyl]-1-propanone;
1-(5-methyl-benzo[b]thien-2-yl)-3-[1-(phenylmethyl)-4-piperidinyl]-1-propanone;
1-(6-methyl-benzo[b]thien-2-yl)-3-[1-(phenylmethyl)-4-piperidinyl]-1-propanone;
1-(3,5-dimethyl-benzo[b]thien-2-yl)-3-[1-(phenylmethyl)-4-piperidinyl]-1-propanone;
1-(benzo[b]thien-2-yl)-3-(1-(phenylmethyl)-4-piperidinyl)-1-propanone;
1-(benzofuran-2-yl)-3-[1-(phenylmethyl)-4-piperidinyl]-1-propanone;
1-(1-phenylsulfonyl-6-methyl-indol-2-yl)-3-[1-(phenylmethyl)-4-piperidinyl]-1-propanone;
1-(6-methyl-indol-2-yl)-3-[1-(phenylmethyl)-4-piperidinyl]-1-propanone;
1-(1-phenylsulfonyl-5-amino-indol-2-yl)-3-[1-(phenylmethyl)-4-piperidinyl]-1-propanone;
1-(5-amino-indol-2-yl)-3-(1-(phenylmethyl)-4-piperidinyl)-1-propanone; and
1-(5-acetylamino-indol-2-yl)-3-(1-(phenylmethyl)-4-piperidinyl)-1-propanone.

Examples of other compounds of the invention are:
1-(6-quinolyl)-3-[1-(phenylmethyl)-4-piperidinyl]-1-propanone;
1-(5-indolyl)-3-[1-(phenylmethyl)-4-piperidinyl]-1-propanone;
1-(5-benzthienyl)-3-[1-(phenylmethyl)-4-piperidinyl]-1-propanone;
1-(6-guinazolyl)-3-[1-(phenylmethyl)-4-piperidinyl]-1-propanone;
1-(6-benzoxazolyl)-3-[1-(phenylmethyl)-4-piperidinyl]-1-propanone;
1-(5-benzofuranyl)-3-[1-(phenylmethyl)-4-piperidinyl]-1-propanone;
1-(5-methyl-benzimidazol-2-yl)-3-[1-(phenylmethyl)-4-piperidinyl]-1-propanone;
1-(6-methyl-benzimidazol-2-yl)-3-[1-(phenylmethyl)-4-piperidinyl]-1-propanone;
1-(5-chloro-benzo[b]thien-2-yl)-3-[1-(phenylmethyl)-4-piperidinyl]-1-propanone;
1-(5-azaindol-2-yl)-3-[1-(phenylmethyl)-4-piperidinyl]-1-propanone;
1-(6-azabenzo[b]thien-2-yl)-3-[1-(phenylmethyl)-4-piperidinyl]-1-propanone;
1-(1H-2-oxo-pyrrolo[2',3',5,6 ]benzo[b]thieno-2-yl)-3-[1-(phenylmethyl)-4-piperidinyl]-1-propanone;
1-(6-methyl-benzothiazol-2-yl)-3-[1-(phenylmethyl)-4-piperidinyl]-1-propanone;
1-(6-methoxy-indol-2-yl)-3-[1-(phenylmethyl)-4-piperidinyl]-1-propanone;
1-(6-methoxy-benzo[b]thien-2-yl)-3-[1-(phenylmethyl)-4-piperidinyl]-1-propanone;
1-(6-acetylamino-benzo[b]thien-2-yl)-3-[1-(phenylmethyl)-4-piperidinyl]-1-propanone; and
1-(5-acetylamino-benzo[b]thien-2-yl)-3-[1-(phenylmethyl)-4-piperidinyl]-1-propanone.

Formula I above includes compounds identical to those depicted but for the fact that one or more hydrogen, nitrogen or carbon atoms are replaced by isotopes thereof (e.g., tritium, carbon-14 or nitrogen-15 isotopes). Such compounds are useful as research and diagnostic tools in metabolism pharmacokinetic studies and in binding assays.

The compounds of formula I may have optical centers and may therefore occur in different isomeric forms. The invention includes all isomers of such compounds having formula I, including mixtures thereof.

DETAILED DESCRIPTION OF THE INVENTION

The preparation of compounds having the formula I is illustrated in the following reaction schemes. Except where otherwise stated, in the reaction schemes and discussion that follow, R$^1$, R$^2$, R$^3$, R$^4$, R$^5$, R$^6$, n, q, p, X, Y and Z and structural formula I are defined as above.

The symbol * (i.e., the asterisk) that appears in several of the structures in the reaction schemes represents, for each structure in which it appears, that the side chain containing the

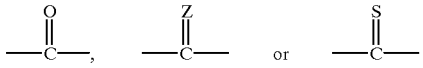

group may optionally be attached to the carbon atom designated by the asterisk rather than to a member of ring A.
All articles, books, patents and patent applications cited in the following discussion are incorporated herein by reference.
Scheme 1
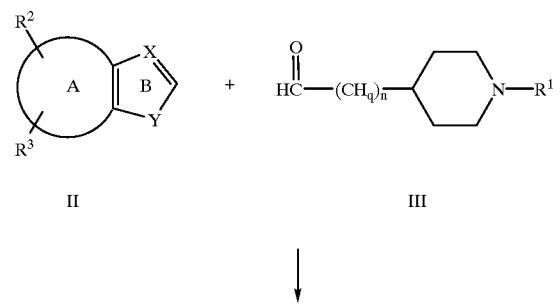
II + III
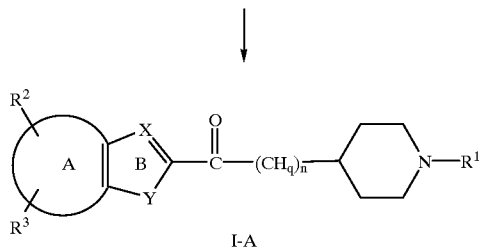
IV
↓
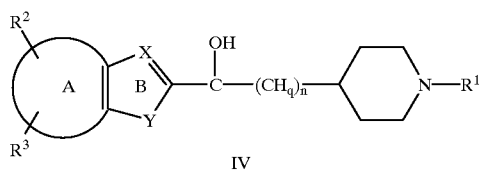
I-A
Scheme 2
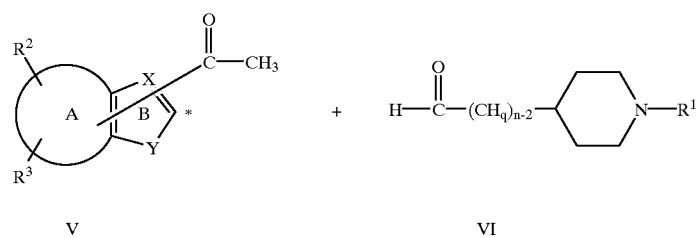
V + VI
↓
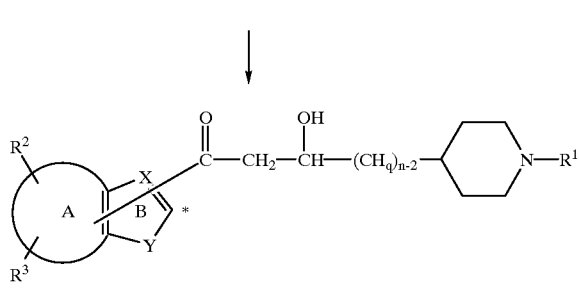
VII
↓
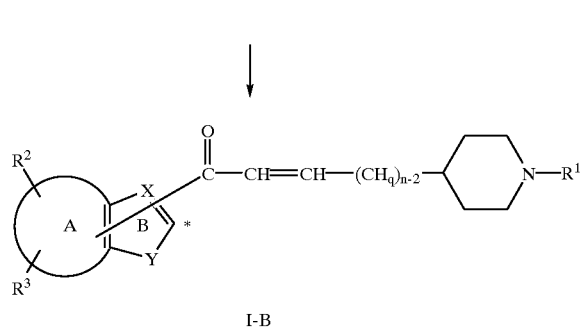
I-B
↓

-continued
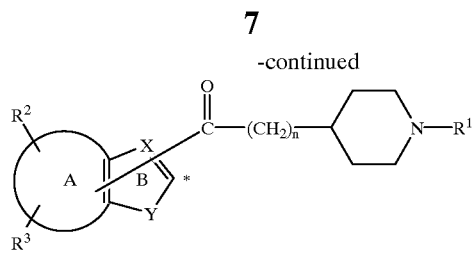
I-A'
Scheme 3
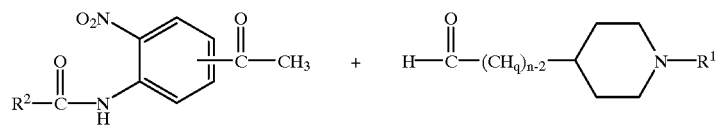
IX                    X
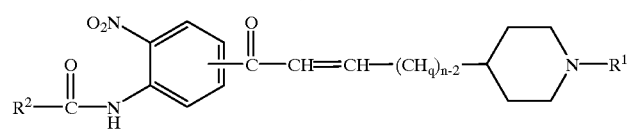
XI
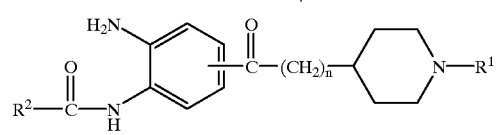
XII
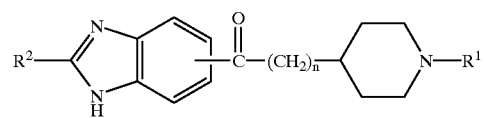
I-C
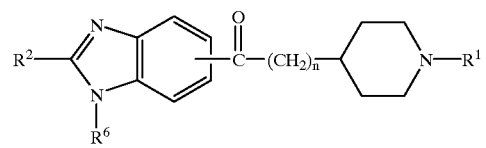
I-D

Scheme 4

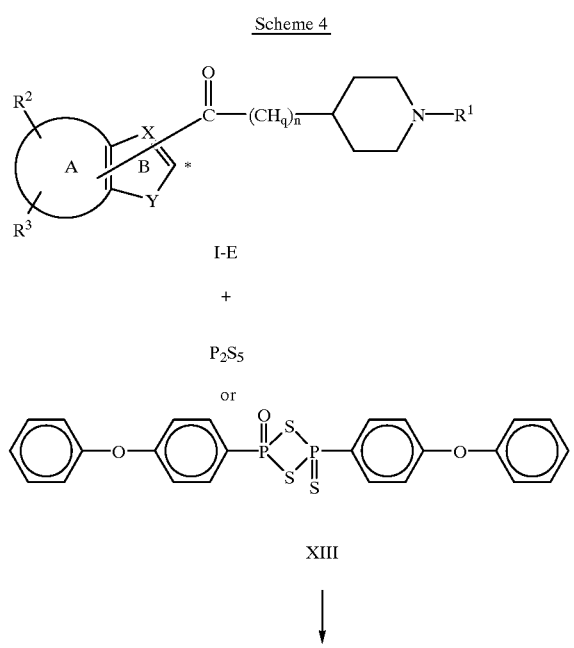

I-E

+

P₂S₅ or

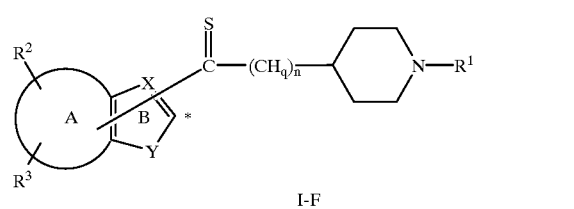

XIII

Scheme 5

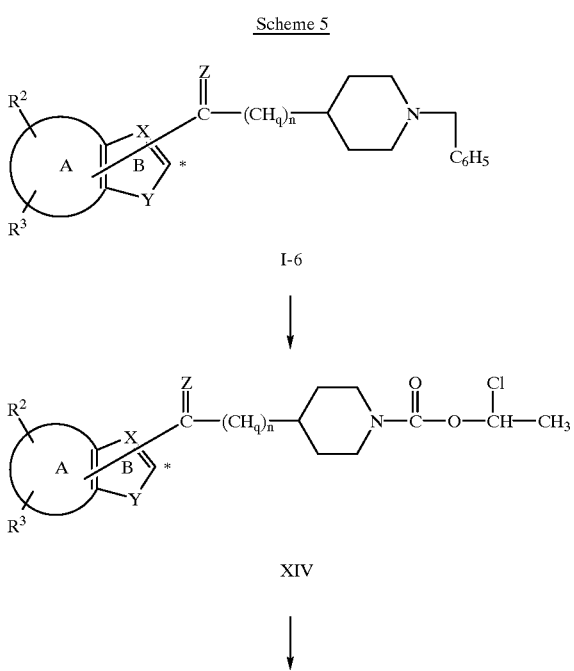

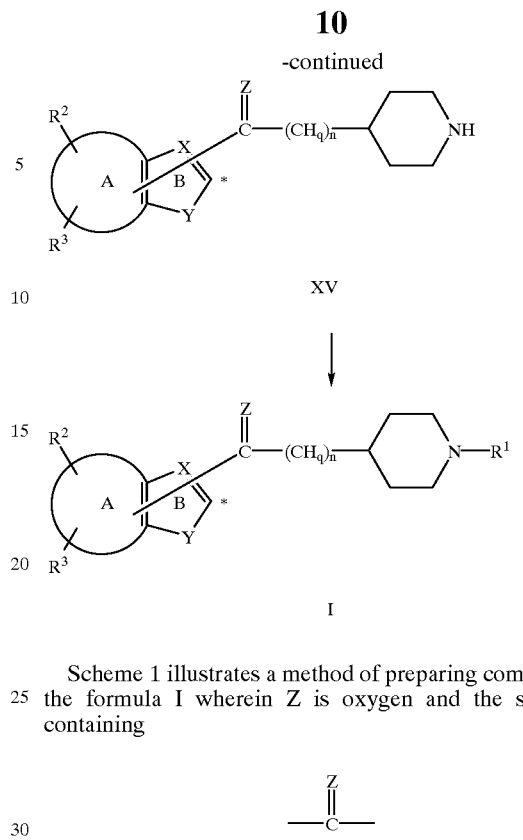

Scheme 1 illustrates a method of preparing compounds of the formula I wherein Z is oxygen and the side chain containing $$-\overset{Z}{\underset{\|}{C}}-$$

is attached to the carbon atom designated by an asterisk in ring B (hereinafter referred to as compounds of the formula I-A).

The starting materials having the formulae II and III are either commercially available or obtainable by synthetic procedures reported in the literature. (See *J. Med. Chem.*, 33, 2777 (1990); *Tetrahedron Letters* 30, 6117 (1989); *Eur. J. Med. Chem.*, 25, 191 (1990); *Heterocycles*, 29, 849 (1989); *J. Org. Chem.*, 47, 757 (1982); *J. Org. Chem.*, 54, 4350 (1989); *Tetrahedron*, 44, 3195 (1988); *Zur. J. Med. Chem. & Chim. Ther.*, 21, 223 (1986); *Chem. Ber.*, 88, 34 (1954); *Tetrahedron*, 28, 2553 (1972); *J. Chem. Soc.* (C), 1733 (1968); U.S. Pat. No. 4,902,694; *J. Heterocyclic Chem.*, 25, 1271 (1988); *Bull. Chem. Soc. Jpn.*, 58, 785 (1986); *J.Ind. Chem. Soc.*, 12, 561 (1975); and *Synthetic Communications*, 14, 947 (1984).

Referring to scheme 1, a compound of the formula II is reacted with the appropriate compound of formula III in the presence of a base to form the corresponding compound of the formula IV. This reaction is usually performed in an appropriate reaction inert solvent at a temperature from about −78° C. to about room temperature, preferably from about −78° C. to about 0° C. Suitable solvents include tetrahydrofuran (THF), ether, toluene, methylene chloride, benzene and dioxane. Suitable bases include lithium bis (trimethylsilyl)amide, lithium diisopropylamide, sodium diisopropylamide, sodium bis(trimethylsilyl)amide, n-butyllithium (n-BuLi), s-butyllithium (s-BuLi) and t-butyllithium (t-BuLi).

The compound of formula IV formed in the foregoing step is then converted into the corresponding compound of formula I-A by reacting it with an oxidizing agent. Examples of oxidizing agents that may be used are manganese dioxide, chromium trioxide and selenium dioxide. Manganese dioxide is preferred. Generally, the oxidation is conducted in a reaction inert solvent at a temperature from about room temperature to about 80° C., preferably from about 50° C. to about 80° C. Examples of suitable solvents are methylene chloride, chloroform, ethyl acetate, benzene and toluene. Preferably, the solvent is methylene chloride or benzene.

Scheme 2 illustrates a method of preparing compounds of the formula I wherein Z is oxygen and n is 2, 3 or 4 (hereinafter referred to as compounds of the formula I-A') and compounds of the formula I wherein n is 2, 3 or 4 and the $(CH_q)_n$ group contains at least one carbon-carbon double bond (hereinafter referred to as compounds of the formula I-B). Referring to scheme 2, the starting materials having the formulae V and VI can be obtained commercially or prepared as described in the literature. (See *J. Org. Chem.*, 54, 4350 (1989); *Tetrahedron*, 44, 3195 (1988); *Chem. Pharm. Bull.*, 39, 181 (1991); *Chem. Ber.*, 119, 2069 (1986); and *J. Ind. Chem. Soc.*, 12, 561 (1975).

As shown in scheme 2, a compound of the formula V is reacted with an aldehyde of the formula VI in the presence of a base to form the corresponding compound of formula VII. Suitable bases for this reaction include sodium hydride, lithium bis(trimethylsilyl)amide, piperidine, pyrrolidine, lithium diisopropylamide, sodium diisopropylamide, n-butyllithium and s-butyllithium. The reaction is usually carried out in a reaction inert solvent such as THF, dimethylformamide (DMF), dioxane, toluene, methylene chloride or ether, with THF, ether or toluene being preferred. The reaction temperature may range from about −78° C. to about 40° C. and is preferably about −78° C. to about 0° C.

If the reaction between compounds of the formulae V and VI is conducted in the presence of a sodium or potassium ($C_1$–$C_5$)alkoxide, it is preferable to use toluene, DMF, THF or methylene chloride as the solvent, with or without a ($C_1$–$C_4$) alcohol, and to conduct the reaction at a temperature from about −40° C. and 80° C., more preferably from about 0° C. to about room temperature.

Subjecting the compound of formula VII so formed to an elimination reaction yields the corresponding compound of formula I-B. The elimination is typically carried out by reacting the compound of formula VII, in the presence of a base, with a reagent capable of forming a leaving group upon reaction with the hydroxy group of formula VII. Appropriate reagents include acetic anhydride, $R^7SO_2Cl$, $R^7COCl$, $R^7OCOCl$ and $R^7NCO$, wherein $R^7$ is selected from ($C_1$–$C_4$) alkyl or phenyl optionally substituted with ($C_1$–$C_6$) alkyl, ($C_1$–$C_4$) alkoxy or nitro. Examples of suitable bases are triethylamine, diisopropylethylamine, diazabicycloundecane (DBU) and diazabicyclononanone. The solvent can be any reaction inert solvent (e.g., methylene chloride, chloroform, THF or toluene). The reaction temperature can range from about 0° C. to about 60° C., and is preferably about 0° C. to about room temperature.

Alternatively, compounds of the formula I-B may be prepared by reacting the appropriate compound of formula VII with the Burgess Inner salt. The Burgess Inner salt may be prepared from chlorosulfonyl isocyanate, methanol and triethylamine, as described in *J. Amer. Chem. Soc.*, 90, 4744 (1968). Generally, this reaction is carried out in an inert solvent such as THF, ether, benzene, toluene or dioxane, preferably THF at a temperature from about room temperature to about the reflux temperature of the solvent, preferably from about 50° C. to about 80° C.

The corresponding compound of the formula I-A' is then prepared by hydrogenation of the compound of formula I-B formed in the above step. Generally, the hydrogenation is accomplished using platinum dioxide or palladium on carbon at a pressure of about 30 psi to about 50 psi. Suitable reaction inert solvents include THF, methanol, ethanol, ethyl acetate and mixtures thereof. Preferably, the solvent is a mixture of ethanol and THF or a mixture of ethanol and ethyl acetate. The reaction temperature may range from about 0° C. to about 60° C. The preferred temperature is about room temperature.

The preparation of compounds having the formulae I-C and I-D are illustrated in scheme 3. Compounds of the formula I-C are those compounds of the formula I wherein ring A is benzo, Y is $NR^6$, $R^6$ is hydrogen, X is nitrogen, $R^3$ is hydrogen and $R^2$ is attached to the carbon atom designated with an asterisk (*) in ring B. Compounds of the formula I-D are those compounds of the formula I wherein ring A is benzo, Y is $NR^6$, $R^6$ is other than hydrogen, X is nitrogen, $R^3$ is hydrogen and $R^2$ is attached to the carbon atom designated with an asterisk (*) in ring B.

Referring to scheme 3, the reaction of a compound of the formula IX with an aldehyde of the formula X to produce a compound of the formula XI is carried out using the procedure depicted in scheme 2 and described above for reaction steps V→VII→I-B→I-A'.

The resulting compound of formula XII is then cyclized in the presence of an acid to afford the corresponding compound of the formula I-C. Examples of acids that may be used are acetic acid, a mixture of acetic acid and a ($C_1$–$C_4$)-alcohol, hydrochloric acid and ether saturated with hydrogen chloride. This reaction is generally conducted at a temperature from about room temperature to about 120° C. Temperatures from about 60° C. to about 90° C. are preferred.

An $R^6$ group may be added to the compound of formula I-C to obtain the corresponding compound having the formula I-D by reacting the appropriate compound of formula I-C with a compound of the formula $R^6L$, wherein L is a leaving group. This reaction is typically carried out in an inert solvent in the presence of a base at a temperature from about −78° C. to about the reflux temperature of the solvent. Suitable bases include sodium hydride, lithium diisopropylamide, t-butyllithium and potassium t-butoxide. Suitable solvents include THF, methylene chloride, benzene, ether, toluene or dioxane. The reaction is preferably conducted in THF in the presence of sodium hydride at a temperature from about 0° C. to about 30° C.

Scheme 4 illustrates the preparation of compounds of the formula I wherein Z is sulfur (hereinafter referred to as compounds of the formula I-F) from compounds of the formula I-E. This transformation is accomplished by reacting the compound of formula I-E with Lawesson's Reagent (2,4-bis(4-methoxyphenyl)-1,3-dithia-2,4-diphosphetane-2,4-disulfide) or phosphorus pentasulfide ($P_2S_5$). Typically, this reaction is conducted in a reaction inert solvent such as THF, acetonitrile, chloroform or toluene at a temperature from about room temperature to about 110° C. It is preferably conducted in THF or toluene at a temperature from about 60° C. to about 80° C.

Compounds of the formula I wherein $R^1$ is other than benzyl may be prepared from the corresponding compounds of the formula I wherein $R^1$ is benzyl (hereinafter referred to as compounds of the formula I-G) as described below and illustrated in scheme 5.

First, a compound of the formula I-G is reacted with a chloroformate of the formula

wherein R⁹ is —ClCHCH$_3$, —CH$_2$CH$_3$ or —CH$_2$C$_6$H$_5$. The preferred reactant is 1-chloroethyl chloroformate. This reaction, which affords the corresponding compound of the formula XIV, is generally carried out in a reaction inert solvent such as methylene chloride, chloroform, dichloroethane, THF or toluene, preferably toluene, at a temperature from about 60° C. to about 100° C., preferably from about 80° C. to about 85° C.

Heating the compound of formula XIV so formed in a (C$_1$–C$_4$) alcohol, preferably methanol or ethanol, yields the corresponding compound of the formula XV. The reaction temperature may range from about 80° C. to about the reflux temperature of the solvent and is preferably about the reflux temperature of the solvent.

The compound of the formula XV formed in the foregoing step is then alkylated and thus converted into the corresponding compound of formula I by reacting it with a compound of the formula R$^1$L, wherein L is a leaving group, in the presence of a base. Examples of suitable leaving groups are chloro, bromo, iodo, mesylate, tosylate and triflate (OTf). Suitable bases include pyridine, triethylamine, dimethylaminopyridine and potassium carbonate. Triethylamine is preferred. Generally, the alkylation is carried out in a reaction inert solvent such as methylene chloride or DMF, at a temperature from about 0° C. to about 100° C., preferably from about room temperature to about 60° C.

In each of the above reactions, pressure is not critical. Pressures in the range of about 0.5 atm to 3 atm are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography.

The compounds of the invention may be administered to a patient by various methods, for example, orally as capsules or tablets, parentally as a sterile solution or suspension, and in some cases, intravenously in the form of a solution. The free base compounds of the invention may be formulated and administered in the form of their pharmaceutically acceptable acid addition salts.

The daily dose of the compounds of the invention is generally in the range of from about 1 to 300 mg/day for the average adult human, and may be administered in single or divided doses.

When incorporated for parenteral administration into a solution or suspension, the compounds of the invention are present in a concentration of at least 1 weight percent, and preferably between about 4–70 weight percent (based on the total weight of the unit). The parenteral dosage unit typically contains between about 5 to 100 mg of active compound(s).

Compounds of the present invention may be administered orally with an inert diluent or an edible carrier, or they may be enclosed in gelatin capsules or compressed into tablets. Such preparations should contain at least 0.5% of active compound(s), but the concentration may vary depending upon the particular form and may be from 4 to 70 weight percent (based on the total weight of the unit). The oral dosage unit typically contains between 1.0 mg to 300 mg of active compound.

The activity of the compounds of the present invention as acetylcholinesterase inhibitors may be determined by a number of standard biological or pharmacological tests. One such procedure for determining cholinesterase inhibition is described by Ellman et al. in "A New and Rapid Colorimetric Determination of Acetylcholinesterase Activity", Biochem. Pharm. 1, 88, (1961).

The present invention is illustrated by the following examples. It will be understood, however, that the invention is not limited to the specific details of these examples. Melting points are uncorrected. Proton nuclear magnetic resonance spectra ($^1$H NMR) and C$^{13}$ nuclear magnetic resonance spectra (C$^{13}$ NMR) were measured for solutions in deuterochloroform (CDCl$_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

EXAMPLE 1

1-[2-(5-Methyl-benzothienyl)]-3-[1-(phenylmethyl)-4-piperidinyl]-2-propen-1-ol

A solution of 5-methyl-benzothiophene (356 mg, 2.4 mmol) in 10 ml of dry tetrahydrofuran (THF) was treated with n-butyllithium (n-BuLi) at −10° C. and the mixture was stirred at room temperature for 30 minutes. A solution of 3-[4-(N-benzylpiperidinyl)]propenal (550 mg, 2.4 mmol) in 5 ml of dry tetrahydrofuran (THF) was added to the reaction mixture at room temperature. After stirring for 30 minutes, the mixture was quenched with water and extracted with chloroform. The organic layer was dried and concentrated to give 750 mg (90%) of desired product.

$^1$H NMR (CDCl$_3$) δ1.3–2.1 (m, 7H), 2.3–2.5 (m, 3H), 2.7–3.0 (m, 2H), 3.47 (s, 2H), 5.37 (d, 1H), 5.6–5.8 (m, 2H), 7.0–7.7 (m, 9H) ppm.

The title compounds of Examples 2–4 were prepared by a method analogous to that described in Example 1.

EXAMPLE 2

1-[2-(6-Methyl-benzothienyl)]-3-[1-(phenylmethyl)-4-piperidinyl]-2-propen-1-ol $^1$H NMR (CDCl$_3$) δ1.3–2.0 (m, 7H), 2.4 (s, 3H), 2.8–2.95 (m, 2H), 3.45 (s, 2H), 5.35 (d, 1H), 5.6–5.8 (m, 2H), 7.0–7.6 (m, 9H) ppm.

EXAMPLE 3

1-[2-(2,5-Dimethyl-benzothienyl)]-3-[1-(phenylmethyl)-4-piperidinyl]-2-propen-1-ol $^1$H NMR (CDCl$_3$) δ1.35–2.0 (m, 7H), 2.3 (s, 3H), 2.5 (s, 3H), 2.8–2.9 (m, 2H), 3.5 (s, 2H), 3.7–3.8 (m, 1H), 5.5–5.9 (m, 3H), 7.0–7.8 (m, 8H) ppm.

EXAMPLE 4

1-(2-Benzothienyl)-3-[1-(phenylmethyl)-4-piperidinyl]-2-propen-1-ol $^1$H NMR (CDCl$_3$) δ1.3–2.0 (m, 7H), 2.7–2.9 (m, 2H), 3.45 (s, 2H), 5.4 (d, 1H), 5.6–5.8 (m, 2H), 7.1 (s, 1H) 7.2–7.3 (m, 7H), 7.65 (dd, 1H), 7.72 (dd, 1H) ppm.

EXAMPLE 5

5-Methyl-benzothien-2-yl-2-[1-(phenylmethyl)-4-piperidinyl]vinyl ketone

A solution of crude 1-[2-(5-methyl-benzothienyl)]-3-[1-(phenylmethyl)-4-piperidinyl]-2-propen-1-ol (750 mg, 2.16 mmol) from Example 1 in 30 ml of benzene was treated with manganese dioxide (1.8 g, 20.7 mmol), and the resulting suspension was heated to reflux for 2 hours. The mixture was cooled to room temperature and filtered through Celite®. The filtrate was concentrated to dryness to give 602 mg of a crude brown semi-solid.

$^1$H NMR (CDCl$_3$) δ1.4–1.9 (m, 4H), 2.0 (dt, 2H), 2.15–2.3 (m, 1H), 2.4 (s, 3H), 2.8–3.0 (m, 2H), 3.5 (s, 2H), 6.8 (s, 0.4H), 6.85 (s, 0.6H), 7.0–7.18 (m, 1H), 7.2–7.9 (m, 9H) ppm.

The title compounds of Examples 6 and 7 were prepared by a method analogous to that described in Example 5.

EXAMPLE 6

2,5-Dimethyl-benzothien-2-yl-2-[1-(phenylmethyl)-4-piperidinyl]vinyl ketone $^1$H NMR (CDCl$_3$) δ1.5–2.0 (m, 4H), 2.1 (dt, 2H), 2.2–2.4 (m, 1H), 2.56 (s, 3H), 2.8 (s, 3H), 2.9–3.05 (m, 2H), 3.56 (s, 2H), 6.72 (s, 0.4H), 6.8 (s, 0.6H), 7.06 (d, 0.6H), 7.1 (d, 0.4H), 7.3–7.8 (m, 8H) ppm.

EXAMPLE 7

Benzothien-2-yl-2-[1-(phenylmethyl)-4-piperidinyl] vinyl ketone $^1$H NMR (CDCl$_3$) δ1.4–1.9 (m, 4H), 1.95–2.1 (dt, 2H), 2.2–2.35 (m, 1H), 2.8–3.0 (m, 2H), 3.54 (s, 2H), 6.86 (s, 0.4H), 6.9 (s, 0.6H), 7.1 (d, 0.6H), 7.15 (d, 0.4H), 7.2–8.0 (m, 10H) ppm.

EXAMPLE 8

1-(5-Methyl-benzo[b]thien-2-yl)-3-[1-(phenylmethyl)-4-piperidinyl]-1-propanone

A solution of crude 5-methyl-benzothien-2-yl 2-[1-(phenylmethyl)-4-piperidinyl)]vinyl ketone from Example 5 (600 mg, 1.6 mmol) in a mixture of ethanol (20 ml) and ethyl acetate (40 ml) was treated with platinum oxide (PtO$_2$) (60 mg) and hydrogenated at 50 psi for 2 hours. (Thin layer chromatography indicated that the reaction was not complete). An additional 45 mg of PtO$_2$ was added and the mixture was hydrogenated for an additional 1 hour. The mixture was filtered through Celite® and the filtrate was concentrated to dryness and purified through chromatography using chloroform to 2% methanol in chloroform as eluent to give 232 mg of the title compound.

$^1$H NMR (CDCl$_3$) δ1.2–2.1 (m, 9H), 2.52 (s, 3H), 2.9–3.0 (m, 2H), 3.05 (t, 2H), 3.52 (s, 2H), 7.2–7.4 (m, 6H), 7.7 (s, 1H), 7.75 (d, 1H), 7.9 (s, 1H) ppm.

The title compounds of Examples 9–11 were prepared by a method analogous to that described in Example 8.

EXAMPLE 9

1-(6-Methyl-benzo[b]thien-2-yl)-3-[1-(phenylmethyl)-4-piperidinyl]-1-propanone $^1$H NMR (CDCl$_3$) δ1.2–2.05 (m, 9H), 2.5 (s, 3H), 2.7–2.8 (m, 2H), 3.0 (t, 2H), 3.5 (s, 2H), 7.2–7.4 (m, 6H), 7.65 (s, 1H), 7.8 (d, 1H), 7.9 (s, 1H) ppm.

EXAMPLE 10

1-(3,5-Diethyl-benzo[b]thien-2-yl)-3-[1-(phenylmethyl)-4-piperidinyl]-1-propanone $^1$H NMR (CDCl$_3$) δ1.2–2.0 (m, 9H), 2.5 (s, 3H), 2.75 (s, 3H), 2.8–3.0 (m, 4H), 3.5 (s, 2H), 7.2–7.8 (m, 8H) ppm.

EXAMPLE 11

1-(Benzothien-2-yl)-3-[1-(phenylmethyl)-4-piperidinyl]-1-propanone $^1$H NMR (CDCl$_3$) δ1.1–2.0 (m, 9H), 2.8–2.95 (m, 2H), 3.05 (t, 2H), 3.5 (s, 2H), 7.2–7.5 (7H), 7.8–7.9 (m, 2H), 7.95 (s, 1H) ppm.

EXAMPLE 12

Benzofuran-2-yl-2-[1-(phenylmethyl)-4-piperidinyl] vinyl ketone

To a solution of diisopropylamine (0.5 ml, 3.6 mmol) in 15 ml of dry THF was added 2.5 M n-butyllithium (1.3 ml, 3.3 mmol) at −78° C. After stirring at −78° C. for 20 minutes, a solution of benzofuran-2-yl methyl ketone (0.48 g, 3 mmol) in 3 ml of dry THF was added at −78° C. and stirred at that temperature for 1.5 hours. The mixture was quenched with water and brine and extracted with ethyl acetate. The organic layer was dried and concentrated to give 1.117 g of product as an oil. The oil was dissolved in 15 ml of methylene chloride and treated with mesyl chloride (0.24 ml, 3 mmol) and triethylamine (0.42 ml, 3 mmol) at room temperature. The mixture was stirred at room temperature overnight, then quenched with water and extracted with methylene chloride. The organic layer was dried and concentrated to give 0.827 g of crude material which was purified through silica gel column chromatography using chloroform to 5% methanol in chloroform as eluent to give 430 mg of off-white crystals.

M.p. 186–188° C.

$^1$H NMR (CDCl$_3$) δ1.8–3.0 (m, 7H), 3.1–3.4 (m, 2H), 4.0 (br s, 2H), 6.9 (s, 0.4H), 6.96 (s, 0.6H), 7.1 (d, 0.6H), 7.15 (d, 0.4H), 7.2–7.7 (m, 10H) ppm.

EXAMPLE 13

Benzofuran-2-yl-3-[1-(phenylmethyl)-4-piperidinyl]-1-propanone

A solution of benzofuran-2-yl 2-[1-(phenylmethyl)-4-piperidinyl]vinyl ketone (410 mg) in a mixture of ethanol (70 ml) and ethyl acetate (40 ml) was treated with platinum oxide (80 mg) and hydrogenated at 45 psi for 1 hour. The mixture was filtered through Celite® and the filtrate was concentrated to dryness to give an off-white solid which was recrystallized from ethyl acetate to give 162 mg of white crystals.

M.p. 199–200° C.

$^1$H NMR (CDCl$_3$) δ1.4–2.2 (m, 7H), 2.4–2.6 (m, 2H), 2.97 (t, 2H), 3.3–3.5 (m, 2H), 4.1 (AB$_q$, 2H), 7.1–7.7 (m, 10H) ppm.

EXAMPLE 14

1-[2-(N-Phenylsulfonyl-6-methyl-indolyl]-3-[1-(phenylmethyl)-4-piperidinyl]-2-propen-1-ol A solution of N-phenylsulfonyl-6-methyl indole (1.18 g, 4.34 mmol) in 30 ml of dry THF was cooled to −78° C. and treated with 3.5 ml (5.2 mmol) of 1.5 M lithium diisopropylamide in cyclohexane at −78° C. After stirring at −78° C. for 1 hour, a solution of 3-[1-(phenylmethyl)-4-piperidinyl]-2-propenal (1.0 g, 4.36 mmol) in 5 ml of dry THF was added at −78° C. and stirred at that temperature for 40 minutes. The mixture was quenched with water and extracted with chloroform. The organic layer was dried and concentrated to give 2.23 g of an orange oil. The oil was purified through silica gel column chromatography using 2% methanol in chloroform as eluent to give 1.0 g of the title compound as a yellow oil.

$^1$H NMR (CDCl$_3$) δ1.4–1.8 (m, 4H), 1.9–2.1 (m, 3H), 2.45 (s, 3H), 2.85–2.95 (m, 2H), 3.3 (br s, 1H), 3.5 (s, 2H), 5.6–5.9 (m, 3H), 6.55 (s, 1H), 7.02 (dd, 1H), 7.2–7.9 (m, 12H) ppm.

EXAMPLE 15

N-Phenylsulfonyl-6-methyl-indol-2-yl-2-[1-(phenylmethyl)-4-piperidinyl]vinyl ketone A solution of 1-[2-(N-phenylsulfonyl-6-methyl-indolyl)]-3-[1-(phenylmethyl)-4-piperidinyl]-2-propen-1-ol (1.2 g, 2.4 mmol) in 30 ml of dry methylene chloride was treated with manganese dioxide (MnO$_2$) (1.0 g, 11.5 mmol). The mixture was stirred for 4 hours under reflux, cooled to room temperature and filtered through Celite®. The filtrate was concentrated to give a yellow oil which was purified through silica gel column chromatography using chloroform to 2.5% methanol in chloroform as eluent to give 740 mg (62% yield) of the title compound as a yellow oil.

$^1$H NMR (CDCl$_3$) δ1.4–1.8 (m, 4H), 1.9–2.1 (m, 2H), 2.15–2.3 (m, 1H), 2.5 (s, 3H), 2.85–3.0 (m, 2H), 3.5 (s, 2H), 6.55 (s, 0.45H), 6.65 (s, 0.55H), 6.9 (d, 0.55H), 6.98 (d, 0.45H), 7.0 (s, 1H), 7.1 (d, 1H), 7.25–7.55 (m, 9H), 7.9–8.1 (m, 3H) ppm.

EXAMPLE 16

1-(1-Phenylsulfonyl-6-methyl-indol-2-yl)-3-[1-(phenylmethyl)-4-piperidinyl]-1-propanone A solution of N-phenylsulfonyl-6-methyl-indol-2-yl-2-[1-(phenylmethyl)-4-piperidinyl]vinyl ketone (360 mg, 7.2 mmol) in a mixture of THF/ethanol (25 ml/25 ml) was treated with platinum oxide (PtO$_2$) (40 mg) and hydrogenated at 45 psi for 75 minutes. The mixture was filtered through Celite®. The filtrate was concentrated to dryness to give a dark oil which was purified though silica gel column chromatography using chloroform as eluent to give 200 mg of the title compound as a yellow oil.

$^1$H NMR (CDCl$_3$) δ1.2–1.75 (m, 7H), 1.8–2.0 (m, 2H), 2.5 (s, 3H), 2.8–3.0 (m, 4H), 3.5 (s, 2H), 7.0 (s, 1H), 7.1 (d, 1H), 7.2–8.0 (m, 12H) ppm.

EXAMPLE 17

1-(6-Methyl-indol-2-yl)-3-[1-(phenylmethyl)-4-piperidinyl]-1-propanone

A suspension of N-phenylsulfonyl-6-methyl-indol-2-yl-2-[1-(phenylmethyl)-4-piperidinyl]ethyl ketone (150 mg) in 20 ml of methanol was treated with 1.5 ml of 2N sodium hydroxide (NaOH), heated at reflux and stirred at that temperature for 70 minutes. The mixture was quenched with water and extracted with chloroform. The organic layer was dried and concentrated to give 100 mg of the title compound as a brown solid.

$^1$H NMR (CDCl$_3$) δ1.2–1.8 (m, 7H), 1.8–2.0 (m, 2H), 2.42 (s, 3H), 2.8–3.0 (m, 4H), 3.5 (s, 2H), 6.95 (d, 1H), 7.1 (s, 1H), 7.2–7.35 (m, 6H), 7.55 (d, 1H) ppm.

EXAMPLE 18

1-(2-Benzothiazolyl)-3-[1-(phenylmethyl)-4-piperidinyl]-2-propen-1-ol

A solution of benzothiazole (0.243 g, 1.8 mmol) in 5 ml of dry THF was treated with 1.5M lithium diisopropylamide in cyclohexane (1.45 ml) at −78° C. and stirred at that temperature for 15 minutes. A solution of 3-[1-(phenylmethyl)-4-piperidinyl]propenal (452 mg, 1.97 mmol) in 3 ml of dry THF was added at −78° C. and stirred at that temperature for 30 minutes. The mixture was quenched with water and extracted with chloroform. The organic layer was dried and concentrated to give a thick yellow oil in a quantitative yield.

$^1$H NMR (CDCl$_3$) δ1.6–2.15 (m, 7H), 2.85–3.0 (m, 2H), 3.5 (s, 2H), 5.5 (d, 1H), 5.7–6.1 (m, 2H), 7.2–7.6 (m, 7H), 7.9 (d, 1H), 8.0 (d, 1H) ppm.

EXAMPLE 19

2-Benzothiazolyl-2-[1-(phenylmethyl)-4-piperidinyl]-vinyl ketone

A solution of 1-(2-benzothiazolyl)-3-[1-(phenylmethyl)-4-piperidinyl]-2-propen-1-ol (654 mg, 1.8 mmol) in 25 ml of methylene chloride was treated with MnO$_2$ (0.782 g, 9 mmol) and heated to reflux. After 3 hours, the mixture was filtered through Celite® and the filtrate was concentrated to give 0.655 mg of a dark oil. The oil was purified through silica gel column chromatography using 2% methanol in chloroform as eluent to give 0.487 g of an amber oil which was solidified upon standing overnight.

$^1$H NMR (CDCl$_3$) δ1.5–1.9 (m, 4H), 2.0–2.15 (m, 2H), 2.3–2.5 (m, 1H), 3.5 (s, 2H), 7.2–7.6 (m, 9H), 8.0 (dd, 1H), 8.2 (dd, 1H) ppm.

EXAMPLE 20

1-(Benzothiazol-2-yl)-3-[1-(phenylmethyl)-4-piperidinyl]-1-propanone

A solution of 2-benzothiazolyl 2-[1-(phenylmethyl)-4-piperidinyl]vinyl ketone (146 mg, 0.4 mmol) in a mixture of ethyl acetate/ethanol (10 ml/10 ml) was treated with PtO$_2$ (20 mg) and hydrogenated at 50 psi for 3 hours. The mixture was filtered through Celite® and the filtrate was concentrated to dryness to give 0.154 g of a dark oil. The oil was purified through silica gel column chromatography using chloroform as eluent to give 37 mg of the title compound as a brown oil.

$^1$H NMR (CDCl$_3$) δ1.2–1.4 (m, 3H), 1.7–1.85 (m, 4H), 1.85–2.1 (m, 2H), 2.8–3.0 (m, 2H), 3.3 (dd, 2H), 3.5 (s, 2H), 7.2–7.4 (m, 5H), 7.45–7.65 (m, 2H), 7.95 (dd, 1H), 8.2 (dd, 1H) ppm.

EXAMPLE 21

N-Phenylsulfonyl-5-nitroindole

A solution of 5-nitroindole (1.62 g, 10 mmol) in 30 ml of dimethylformamide (DMF) was treated with 60% sodium hydride (0.44 g, 11 mmol) at room temperature. After 3 minutes, benzenesulfonyl chloride (1.766 g, 10 mmol) was added. The mixture was stirred at room temperature overnight and treated with 250 ml of water. A precipitate formed and was filtered to give a yellow solid which was pumped in vacuo to give 2.7 g (89%) of the title compound.

$^1$H NMR (CDCl$_3$) δ6.82 (d, 1H), 7.45–7.55 (m, 2H), 7.6 (d, 1H), 7.72 (d, 1H), 7.9 (m, 2H), 8.1 (d, 1H), 8.2 (dd, 1H), 8.5 (d, 1H) ppm.

EXAMPLE 22

N-Phenylsulfonyl-5-nitroindol-2-yl-2-[1-(phenylmethyl)-4-piperidinyl]vinyl ketone A solution of N-phenylsulfonyl-5-nitroindole (646 mg, 2.14 mmol) in 10 ml of dry THF was treated with lithium diisopropylamide (1.5M in cyclohexane) (1.7 ml, 2.6 mmol) at −78° C. After 1 hour at −78° C., a solution of 3-[4-(N-phenylmethylpiperidinyl)]propenal (490 mg, 2.14 mmol) in 2 ml of dry THF was added at −78° C. After 40 minutes at −78° C., the mixture was quenched with water and extracted with methylene chloride. The organic layer was dried and concentrated to give 1.149 g of a yellow oil. The oil was dissolved in 30 ml of benzene, treated with $MnO_2$ (1.86 g, 21.4 mmol) and heated at reflux for 4 hours. An additional 900 mg of $MnO_2$ was added and the mixture was heated at reflux overnight. The mixture was filtered through Celite® and the filtrate was concentrated to give a brown oil which was purified through silica gel column chromatography using chloroform as eluent to give the title compound as a brown oil.

$^1$H NMR (CDCl$_3$) δ1.45–1.95 (m, 4H), 1.95–2.1 (m, 2H), 2.15–2.4 (m, 1H), 2.9–3.05 (m, 2H), 3.55 (s, 2H), 6.55 (s, 0.5H), 6.62 (s, 0.5H), 6.98 (d, 0.5H), 7.05 (d, 1H), 7.1 (s, 1H), 7.2–7.4 (m, 4H), 7.5–7.7 (m, 4H), 8.05–8.15 (m, 2H), 8.2–8.4 (m, 2H), 8.5 (d, 1H) ppm.

EXAMPLE 23

N-Phenylsulfonyl-5-nitroindol-2-yl-2-[1-(phenylmethyl)-4-piperidinyl]ethyl ketone A solution of N-phenylsulfonyl-5-nitroindol-2-yl 2-[1-(phenylmethyl)-4-piperidinyl]vinyl ketone (187 mg, 0.35 mmol) in a mixture of ethyl acetate/ethanol (20 ml/8 ml) was treated with PtO$_2$ (50 mg) and hydrogenated at 40 psi for 1.5 hours. The mixture was filtered through Celite® and the filtrate was concentrated to give 177 mg (100%) of a brown oil.

$^1$H NMR (CDCl$_3$) δ1.1–2.0 (m, 9H), 2.75–2.9 (m, 2H), 2.92 (t, 2H), 3.42 (s, 2H), 6.68 (d, 1H), 6.72 (dd, 1H), 6.8 (s, 1H), 7.1–7.5 (m, 8H), 7.7–7.9 (m, 3H) ppm.

EXAMPLE 24

5-Nitroindol-2-yl 2-[1-(phenylmethyl)-4-piperidinyl] ethyl ketone

A solution of N-phenylsulfonyl-5-nitroindol-2-yl 2-[1-(phenylmethyl)-4-piperidinyl]ethyl ketone (160 mg, 0.32 mmol) in 3 ml of methanol and 2 ml of 2N NaOH was heated at reflux for 2 hours. The mixture was concentrated to dryness and the residue was diluted with brine and extracted with chloroform. The organic layer was dried and concentrated to dryness to give 144 mg of a brown solid which was purified through silica gel column chromatography to give 31 mg of the title compound as a brown solid.

$^1$H NMR (CDCl$_3$) δ1.1–2.0 (m, 9H), 2.8–3.0 (m, 4H), 3.5 (s, 2H), 6.76 (dd, 1H), 6.9 (s, 1H), 6.96 (s, 1H), 7.1–7.3 (m, 6H) ppm.

EXAMPLE 25

1-(1-Ethyl-2-methyl-1H-benzimidazol-5-yl)-3-[(1-phenylmethyl)-4-piperidinyl]-2-propen-1-one A mixture of 0.1 g (0.5 mM) of 1-ethyl-2-methylbenzimidazole-5-yl methyl ketone and 0.1 g (0.5 mM) 4-formyl-N-benzylpiperidine in 10 mL of tetrahydrofuran (THF) was cooled to −78° C. under a nitrogen atmosphere. To this mixture were added dropwise 0.5 mL (0.5 mM) of a 1M solution of lithium bis(trimethylsilyl)amide in THF. The reaction was stirred at −78° C. for 1 hour, then warmed to room temperature. To the reaction was added 10 mL of water and the pH was adjusted to 2.0 with 1N hydrochloric acid (HCl). The mixture was extracted with 15 mL of ethyl acetate. The pH of the water layer was then sequentially adjusted to 3.0, 4.0, 5.0, 6.5, and 8.5 with 1N NaOH, each time extracting with 15 mL of ethyl acetate. The ethyl acetate extracts at pH=5.0 and 6.5 were combined, dried with sodium sulfate (Na$_2$SO$_4$) and evaporated to yield 50 mg (26%) of the title compound as an oil.

Thin layer chromatography (TLC) (10:1 CHCl$_3$:CH$_3$OH), R$_f$=0.58.

$^1$H NMR (CDCl$_3$) δ8.22 (s, 1H), 7.88 (d, 1H), 7.30 (m, 5H), 6.90 (m, 3H), 4.14 (q, 2H), 3.50 (s, 2H), 3.05 (m, 2H), 2.85 (m, 2H), 2.61 (s, 3H), 1.4–2.1 (m, 5H), 1.40 (t, 3H).

EXAMPLE 26

1-(1-Ethyl-2-methyl-1H-benzimidazol-5-yl)-3-[1-(phenylmethyl)-4-piperidinyl]-1-propanone hydrochloride To a solution of the title compound from Example 25 0.14 g (0.36 mM) in 20 mL of ethanol were added 10 mg of PtO$_2$ and the mixture was hydrogenated at 50 psi for 1 hour. The reaction was filtered and the ethanol solvent evaporated. The residue was suspended in 50 mL of a 1:1 mixture of ethyl acetate: H$_2$O, and the pH adjusted to 8.5 with 1N sodium hydroxide (NaOH). The ethyl acetate layer was dried (Na$_2$SO$_4$) and evaporated to yield 0.1 g (72%) of the free base of the title compound as an oil.

TLC (10:1 CHCl$_3$:CH$_3$OH), R$_f$=0.64.

$^1$H NMR (CDCl$_3$) δ8.26 (s, 1H), 7.92 (d, 1H), 7.28 (m, 6H), 4.18 (q, 2H), 3.48 (s, 2H), 3.05 (m, 2H), 2.85 (m, 2H), 2.54 (s, 3H), 1.4–2.0 (m, 9H), 1.30 (t, 3H).

The oil was dissolved in ethyl acetate and to this solution was added dropwise a solution of HCl dissolved in ether. The resulting precipitate was filtered and triturated with hexanes to yield 0.105 g of the title compound as a hygroscopic white solid.

M.p.=165–167° C.

Mass spectrum: 389.2 (p), 298.0 (p−91), 172.0 (p−217), 90.9 (p−298, base peak).

EXAMPLE 27

1-(2-Methyl-6-benzothiazolyl)-3-[1-(phenylmethyl)-4-piperidinyl]-2-propen-1-one

A mixture of 0.191 g (0.001 M) of 2-methyl-6-benzothiazolyl methyl ketone (prepared as described by S. S. Sawhney, J. Singh, and O. P. Bansal, *J. Ind. Chem. Soc.,* 12, 561 (1975)) and 0.203 g (0.001 M) of 4-formyl-N-benzyl piperidine in 5 mL of THF was cooled to −78° C. under a nitrogen atmosphere. To this solution were added dropwise 0.73 mL (0.0011 M) of lithium diisopropylamide (1.5 M solution in THF). The reaction was stirred at −78° C. for 1 hour and then warmed to 0° C. The reaction was quenched with 5 mL of water and extracted with ethyl acetate. The ethyl acetate extracts were dried (Na$_2$SO$_4$) and evaporated to yield 0.4 g of a brown gum. This residue was chromatographed on 30 g of silica gel using a 98:2 mixture of CH$_2$Cl$_2$:CH$_3$OH as the eluant. Appropriate fractions were combined to yield 0.122 g (32%) of the title compound as an amorphous solid. TLC (10:1 CH$_2$Cl$_2$:CH$_3$OH) R$_f$=0.63.

$^1$H NMR (CDCl$_3$) δ8.42 (s, 1H), 7.9 (m, 2H), 7.35–7.5 (m, 5H), 6.8–7.1 (m, 2H), 3.52 (s, 2H), 2.95 (m, 2H), 2.8 (s, 3H), 1.4–2.5 (m, 7H).

Mass spectrum: 376.1600. Calc'd for CH$_{23}$H$_{24}$N$_2$OS: ±2.6 ppm.

EXAMPLE 28

1-(2-Methyl-6-benzothiazolyl)-3-[1-(phenylmethyl)-4-piperidinyl]-1-propanone hydrochloride A solution of 0.120 g (0.319 mM) of the free base of the title compound from Example 27 was dissolved in 50 mL of ethanol. To this was added 50 mg of $Pt_2O$ and the mixture hydrogenated at 50 psi for 1 hour. The reaction was filtered and the ethanol was evaporated to yield 0.112 g (100%) of the title compound (free base) as an amorphous solid.

TLC (10:1 $CH_2Cl_2$:$CH_3OH$) $R_f$=0.5.

$^1$H NMR ($CDCl_3$) δ8.45 (s, 1H), 8.02 (dd, 2H), 7.25 (m, 5H), 3.5 (s, 2H), 3.02 (m, 2H), 2.85 (m, 2H), 2.83 (s, 3H), 1.4–2.0 (m, 9H).

Mass spectrum: 378 (p), 287 (p−91), 172 (p−206), 91 (p−287, base peak).

This residue was dissolved in 15 mL of ethyl acetate to which was added HCl dissolved in ethyl acetate (EtOAc). The resulting precipitate was filtered and dried under vacuum to yield 92 mg (70%) of the title compound.

M.p.=110°–112° C.

EXAMPLE 29

N-Acetyl-4-aminoacetophenone

A mixture of 5.0 g (0.37 M) of 4-aminoacetophenone, 3.8 mL (0.04 M) of acetic anhydride, and 5.5 mL (0.04 M) of triethylamine were dissolved in 50 mL of methylene chloride ($CH_2Cl_2$) and stirred at room temperature for 18 hours. A white solid precipitated from the solution and was collected by filtration. The solid was washed with water and air dried to yield 3.32 g (49%) of N-acetyl-4-aminoacetophenone.

TLC (1:1 $CHCl_3$:EtOAc) $R_f$=0.61.

$^1$H NMR ($CDCl_3$) δ8.58 (br s, 1H), 7.90 (d, 2H), 7.64 (d, 2H), 2.56 (s, 3H), 2.19 (s, 3H).

EXAMPLE 30

N-Benzoyl-4-aminoacetophenone

A mixture of 5.0 g (0.37 M) of 4-aminoacetophenone, 4.7 mL (0.04 M) of benzoyl chloride, and 5.5 mL (0.04 M) of triethylamine were dissolved in 50 mL of methylene chloride ($CH_2Cl_2$) and stirred at room temperature for 18 hours. The resulting precipitate was filtered and washed with water. The residue was dissolved in chloroform ($CHCl_3$) and dried with $Na_2SO_4$. Evaporation of the $CHCl_3$ yielded 4.2 g (47%) of N-benzoyl-4-aminoacetophenone.

M.p.=206°–208° C.

$^1$H NMR ($CDCl_3$+DMSO) δ9.58 (br s, 1H), 7.80 (m, 6H), 7.34 (m, 3H), 2.44 (s, 3H).

EXAMPLE 31

N-Acetyl-3-nitro-4-aminoacetophenone

To 10 mL of fuming nitric acid cooled to 0° C. was added portionwise 1.0 g (5.6 mM) of N-acetyl-4-aminoacetophenone. The temperature was maintained below 5° C. to prevent excess nitration of the benzene ring. The solution was stirred for 15 minutes at 0° C. and then carefully poured onto ice. A yellow solid precipitated and was collected by filtration to yield 0.42 g (34%) of the title compound.

TLC (2:1 $CHCl_3$:EtOAc) $R_f$=0.78.

$^1$H NMR ($CDCl_3$) δ8.9 (d, 1H), 8.77 (s, 1H), 8.16 (s, 1H), 2.64 (s, 3H), 2.34 (s, 3H).

EXAMPLE 32

N-Benzoyl-3-nitro-4-aminoacetophenone

To 10 mL of fuming nitric acid cooled to −5° C. were added portionwise 2.5 g (0.01 M) of N-benzoyl-4-aminoacetophenone. The temperature was maintained below 0° C. The reaction was stirred for 10 minutes and the resulting solution poured onto ice. A yellow solid precipitate was former which was collected by filtration. The solid was dissolved in $CHCl_3$ and chromatographed on silica gel using $CHCl_3$ as the elutant. Appropriate fractions were combined and evaporated to yield 1.0 g (35%) of the title compound as a yellow solid.

$^1$H NMR ($CDCl_3$) δ9.12 (d, 1H), 8.84 (s, 1H), 8.25 (d, 1H), 7.96 (d, 2H), 7.6 (m, 3H), 2.66 (s, 3H).

EXAMPLE 33

3-[1-(1-Phenylmethyl)-4-piperidinyl]-1-(3-nitro-4-acetamido-phenyl)2-propen-1-one A solution of 2.6 g (11.7 mM) of N-acetyl-3-nitro-4-aminoacetophenone in 25 mL of THF was cooled to −60° C. under a nitrogen atmosphere. To the solution were added 4.7 mL (11.7 mM) of N-butyllithium (2.5 M in hexanes), maintaining the temperature below −60° C. The reaction was stirred for 15 minutes. A solution of 4-formyl-N-benzylpiperidine dissolved in 5 mL of THF was added dropwise, maintaining the reaction temperature below −55° C. The reaction was stirred for 1 hour and then warmed to room temperature. At room temperature, the reaction was quenched with 10 mL of water and extracted with ethyl acetate. The ethyl acetate extracts were combined, dried ($Na_2SO_4$) and evaporated to yield a dark oil. This oil was chromatographed on silica gel using 5:1 $CHCl_3$:EtOAc as the elutant. Appropriate fractions were combined to yield 1.2 g (25%) of the title compound as an oil which slowly crystallized.

TLC (10:1 $CHCl_3$:$CH_3OH$), $R_f$=0.45.

$^1$H NMR ($CDCl_3$) δ8.90 (d, 1H), 8.76 (s, 1H), 8.14 (d, 1H), 8.30 (m, 5H), 3.53 (s, 2H), 2.94 (m, 2H), 2.32 (s, 3H), 1.5–2.15 (m, 5H).

EXAMPLE 34

3-[1-(Phenylmethyl)-4-piperidinyl]-1-(3-nitro-4-benzoyl-amidophenyl)2-propen-1-one A solution of 0.80 g (2.90 mM) of the title compound from Example 32 in 30 mL of anhydrous THF was cooled to −70° C. under a nitrogen atmosphere. To the solution were added 1.2 mL (2.9 mM) of N-butyllithium (2.5 M solution in hexanes) dropwise, forming a dark solution. The solution was stirred at −70° for 10 minutes. To this mixture was added dropwise a solution of 0.6 g (2.9 mM) of 4-formyl-N-benzylpiperidine in 10 mL of THF. The reaction was slowly warmed to room temperature and stirred for 18 hours. The reaction mixture was quenched with 25 mL of water and extracted with ethyl acetate. The ethyl acetate extracts were dried ($Na_2SO_4$) and evaporated. The residue was chromatographed on silica gel using 1:1 $CHCl_3$:EtOAc as the eluent. Appropriate fractions were combined to yield 0.45 g (34%) of the title compound as an amorphous solid.

TLC (10:1 $CHCl_3$:$CH_3OH$), $R_f$=0.67.

¹H NMR (CDCl₃) δ9.14 (d, 1H), 8.82 (s, 1H), 8.22 (d, 1H), 7.98 (d, 2H), 7.55 (m, 3H), 7.32 (m, 5H), 7.10 (m, 1H), 6.85 (m, 1H), 3.54 (s, 1H), 2.95 (m, 2H), 1.4–2.3 (m, 7H).

EXAMPLE 35

1-(3-Amino-4-acetamidophenyl)-3-[(1-phenylmethyl)-4-piperidinyl]-1-propanone

To a solution of 0.9 g (2.2 mM) of the title compound from Example 33 in 50 mL of ethanol were added 20 mg of PtO₂, and the mixture was hydrogenated at 50 psi for one hour. The mixture was filtered and the ethanol evaporated to yield 0.9 g (100%) of the title compound as an oil.

¹H NMR (CDCl₃) δ7.6 (s, 1H), 7.2–7.5 (m, 7H), 3.5 (s, 2H), 2.85 (m, 4H), 2.21 (s, 3H), 1.2–2.0 (m, 9H).

Mass spectrum: 379.2 (p), 202.3 (p–176.9), 172.3 (p–206.9), 91.0 (p–288.3, base peak).

EXAMPLE 36

1-(2-Methyl-1H-benzimidazol-5-yl)-3-[1-(phenylmethyl)-4-piperidinyl]-1-propanol hydrochloride A solution of 0.6 g (1.6 mM) of the free base of the title compound from Example 35 in 10 mL of acetic acid was heated on a steam bath (80°–90° C.) for 1 hour. The acetic acid was evaporated and the residue dissolved in 25 mL of ethyl acetate. To this was added 25 mL of water and the pH was adjusted to 3.0. The ethyl acetate layer was separated from the water layer and the water layer was sequentially adjusted to pH=5.0, 6.0, and 9.0, each time extracting with ethyl acetate. The pH=9.0 ethyl acetate extract was dried (Na₂SO₄) and evaporated to afford 0.4 g (69%) of the free base of the title compound (free base).

¹H NMR (CDCl₃) δ8.08 (s, 1H), 7.80 (s, 1H), 7.47 (m, 1H), 7.25 (m, 6H), 3.47 (s, 2H), 2.8–3.0 (m, 4H), 2.59 (s, 3H), 1.90 (t, 2H), 1.64 (m, 4H), 1.25 (m, 3H).

TLC (10:1:0.1 CHCl₃:CH₃OH:NH₄OH), R$_f$ (free base)= 0.50.

The amorphous solid was dissolved in ethyl acetate and to this was added an ether solution of hydrogen chloride (HCl). The resulting precipitate was filtered and dried to yield 0.26 g (62%) of the title compound as a tan solid.

Mass spectrum: 361.3 (p), 270.2 (p–91.1), 172.3 (p–189), 91.1 (0–270.2, base peak).

EXAMPLE 37

1-(3-Amino-4-benzoylamidophenyl)-3-[(1-phenylmethyl)-4-piperidinyl]-1-propanone

To a solution of 0.45 g (1.0 mM) of the title compound from Example 34 in 50 mL of ethanol were added 25 mg of PtO₂ and the mixture was hydrogenated at 50 psi for 1 hour. After filtration to remove the catalyst, the ethanol was evaporated to yield the title compound as an amorphous solid.

¹H NMR (CDCl₃) δ8.15 (s, 1H), 7.90 (d, 2H), 7.2–7.7 (m, 10H), 3.88 (br s, 2H), 3.50 (s, 2H), 2.90 (m, 4H), 1.2–2.0 (m, 9H).

This material was used in the procedure of Example 38 without further purification.

EXAMPLE 38

1-(2-Phenyl-1H-benzimidazol-5-yl)-3-[(1-phenylmethyl)-4-piperidinyl]-1-propanone hydrochloride The title compound of Example 37 was dissolved in a 50:50 mixture of ethanol and acetic acid and heated to 75° C. for 3 hours. The reaction was cooled to room temperature and diluted with water. The pH of the mixture was adjusted to 9.5 and the mixture was extracted with ethyl acetate. The ethyl acetate extracts were dried (Na₂SO₄) and evaporated to yield 0.19 g (45%) of the free base of the title compound.

TLC (10:1:0.1 CHCl₃:CH₃OH:NH₄OH), R$_f$=0.40.

¹H NMR (CDCl₃) δ8.14 (d, 2H), 7.86 (d, 1H), 7.2–7.6 (m, 1H), 3.58 (s, 2H), 2.92 (m, 4H), 1.2–2.1 (m, 9H).

The residue was dissolved in ethyl acetate, and to this solution was added dropwise an ether solution of HCl. The resulting precipitate was collected via filtration and dried to yield the title compound as a tan solid.

M.p.>300° C.

Mass spectrum: 424.2 (p+1).

EXAMPLE 39

1-(2-Methyl-6-benzthiazolyl)-3-(4-piperidinyl)-1-propanone

A mixture of 0.90 g (2.38 mM) of 1-(2-methyl-6-benzthiazolyl)-3-[1-(phenylmethyl)-4-piperidinyl]-1-propanone (Example 27) and 0.33 mL (3.1 mM) of 1-chloroethyl chloroformate was refluxed in 10 mL of 1,2-dichloroethane for 2 hours. The resulting brown solution was cooled to room temperature and diluted with 15 mL of water. This mixture was extracted twice with 20 mL of ethyl acetate. The ethyl acetate extracts were combined, dried (Na₂SO₄), and evaporated to yield 1.0 g (100%) 1-(2-methyl-6-benzothiazolyl)-3-[(1-chloroethylformyl)-4-piperidinyl]-1-propanone as an oil.

TLC (10:1 CH₂Cl₂:CH₃OH) R$_f$=0.86.

¹H NMR (CDCl₃) δ8.4 (s, 1H), 7.9 (m, 2H), 6.55 (q, 1H), 2.65–3.2 (m, 4H), 2.77 (s, 3H), 1.83 (d, 3H), 1.4–1.95 (m, 9H). ¹³C NMR (CDCl₃, ppm) 198.1, 171.3, 155.8, 137.4, 135.8, 133.4 125.9, 122.1, 122.0, 83.3, 44.2 (2), 35.7, 35.3, 32.0, 30.4 (2), 25.4, 20.3.

A methanol solution (5 mL) of 0.9 g (2.28 mM) of the above oil was refluxed for 1 hour. Upon cooling, a yellow precipitate formed. This precipitate was dissolved in 4N HCl and the solution extracted with ether. The HCl solution was adjusted to pH 9 with sodium carbonate (Na₂CO₃) and extracted with ethyl acetate. The ethyl acetate extracts were dried (Na₂SO₄), and evaporated to yield 0.250 g (38%) of the title compound as an amorphous yellow solid.

TLC (10:1 CH₂Cl₂:CH₃OH) R$_f$=0.01.

¹H NMR (CDCl₃) δ8.5 (s, 1H), 7.95 (m, 2H), 32 (m, 2H), 2.85 (s, 1H), 2.6 (m, 2H), 1.1–1.8 (m, 9H). ¹³C NMR (CDCl₃, ppm) 198.1, 156.3, 136.0 (2), 132.0, 125.9, 122.3, 122.1, 46.4 (2), 35.8, 35.7, 33.0, 31.4 (2), 20.5.

EXAMPLE 40

1-(2-Methyl-6-benzothiazolyl)-3-[1-(2-methyl-4-thiazolyl)methyl]-4-piperidinyl]-1-propanone hydrochloride A mixture of 250 mg (0.87 mM) of the title compound of Example 39, 0.160 mg (0.87 mM) of 2-methyl-4-chloromethyl thiazole and 0.36 mL (2.60 mM) of triethylamine was refluxed in 5 mL methylene chloride for 12 hours. The reaction was cooled to room temperature and diluted with 10 mL of water. The mixture was extracted with ethyl acetate, and the ethyl acetate extracts combined, dried (Na₂SO₄), and evaporated to yield 0.27 g of a yellow gum. This material was chromatographed on 10 g of silica gel using 98:2 CHCl₃:CH₃OH as an elutant. Appropriate fractions were combined and evaporated to yield 100 mg (29%) of the title compound as a yellow amorphous solid.

TLC (10:1 $CH_2Cl_2$:$CH_3OH$), $R_f$=0.21.

$^1$H NMR ($CDCl_3$) δ8.50 (s, 1H), 7.9 (m, 2H), 6.87 (s, 1H), 3.62 (s, 2H), 3.0 (m, 4H), 2.87 (s, 3H), 2.69 (s, 3H), 2.0 (t, 2H), 1.7 (m, 4H), 1.35 (m, 3H).

Mass Spectrum: 399.2 (p), 287.2 (p–112, base peak), 223.1 (p–176.1), 193.1 (p–206.1), 176.0 (p–223), 112.0 (p–287), 71.0 (p–328).

This material was dissolved in ethyl acetate and to it was added an ether solution of HCl gas. The resulting precipitate was filtered and recrystallized from $CH_2Cl_2$/ether to yield 92 mg of the title compound.

M.p.=184°–186° C.

EXAMPLE 41

1-(5-Amino-indol-2-yl)-3-[1-(phenylmethyl)-4-piperidinyl]-1-propanone

A solution of 1-(1-Phenylsulfonyl-5-amino-indol-2-yl)-3-(N-phenylmethylpiperidin-4-yl)-1-propanone (160 mg, 0.32 mmol) in 3 ml of methanol and 2 ml of 2N NaOH was heated at reflux for 2 hours. The mixture was concentrated to dryness and the residue was diluted with brine and extracted with chloroform. The organic layer was dried and concentrated to dryness to give 144 mg of brown solid which was purified through silica gel column chromatography to give 31 mg of the title compound as a brown solid.

$^1$H NMR ($CDCl_3$) δ1.1–2.0 (m, 9H), 2.8–3.0 (m, 4H), 3.5 (s, 2H), 6.76 (dd, 1H), 6.9 (s, 1H), 6.96 (s, 1H), 7.1–7.3 (m, 6H)ppm.

EXAMPLE 42

1-(5-N-acetylamino-indol-2-yl)-3-[1-(phenylmethyl)-4-piperidinyl]-1-propanone

A solution of 1-(5-amino-indol-2-yl)-3-[1-(phenylmethyl)-4-piperidinyl]-1-propanone (18 mg, 0.05 mmol) in 0.5 ml of methylene chloride was treated with a solution of triethylamine (6 mg, 0.06 mmol) in 0.5 ml of methylene chloride and a solution of acetyl chloride (4.7 mg, 0.06 mmol) in 0.5 ml of methylene chloride at room temperature and the mixture was stirred at room temperature for 4 hours. The mixture was quenched with water and extracted with methylene chloride. The organic layer was dried and concentrated to give 11 mg of the title compound.

$^1$H NMR ($CDCl_3$) δ1.2–2.1 (m, 9H), 2.2 (s, 3H), 2.8–3.0 (m, 4H), 3.5 (s, 2H), 7.0–7.65 (m, 9H), 8.0 (s, 1H), 9.35 (s, 1H) ppm.

What is claimed is:

1. A compound of the formula

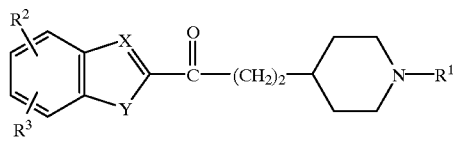

wherein $R^1$ is benzyl, methoxybenzyl, fluorobenzyl or a group of the formula

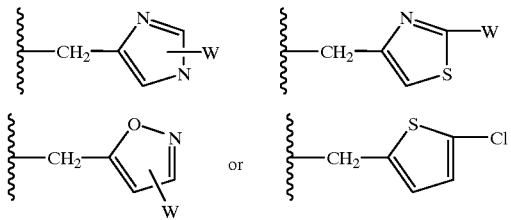

wherein W is hydrogen, $(C_1$–$C_6)$alkyl, phenyl or benzyl;

$R^2$ and $R^3$ are independently selected from $(C_1$–$C_4)$alkyl, chloro, fluoro, methoxy, amino and —NHC(=O)$CH_3$;

X is CH or CCH$_3$;

Y is NR$^6$; and $R^6$ is hydrogen, $(C_1$–$C_6)$alkyl, CO$(C_1$–$C_6)$alkyl, or SO$_2$-phenyl, wherein the phenyl moiety of said SO$_2$-phenyl may optionally be substituted with from one to five substituents independently selected from $(C_1$–$C_4)$ alkyl;

or a pharmaceutically acceptable salt of such compound.

2. A compound according to claim 1 wherein Y is NH or NCH$_3$; and R$^1$ is benzyl.

3. A compound according to claim 2 wherein R$^2$ and R$^3$ are independently selected from the group consisting of $(C_1$–$C_4)$alkyl, chloro, amino and —NHC(=O)$CH_3$.

4. A compound according to claim 1 selected from the group consisting of:
1-(1-phenylsulfonyl-6-methyl-indol-2-yl)-3-[1-(phenylmethyl)-4-piperidinyl]-1-propanone;
1-(6-methyl-indol-2-yl)-3-[1-(phenylmethyl)-4-piperidinyl)-1-propanone;
1-(1-phenylsulfonyl-5-amino-indol-2-yl)-3-[1-(phenylmethyl)-4-piperidinyl)-1-propanone;
1-(5-amino-indol-2-yl)-3-[1-(phenylmethyl)-4-piperidinyl]-1-propanone; and
1-(5-acetylamino-indol-2-yl)-3-[1-(phenylmethyl)-4-piperidinyl]-1-propanone.

5. A pharmaceutical composition for enhancing memory or treating or preventing Alzheimer's disease comprising a compound according to claim 1 and a pharmaceutically acceptable carrier.

6. A pharmaceutical composition for inhibiting cholinesterase in a mammal comprising a compound according to claim 1 and a pharmaceutically acceptable carrier.

7. A method of inhibiting cholinesterase in a mammal comprising administering to said mammal a cholinesterase inhibiting amount of a compound according to claim 1.

8. A method of enhancing memory or treating or preventing Alzheimer's disease comprising administering to a patient a memory enhancing effective amount of a compound according to claim 1.

9. A compound of the formula (I)

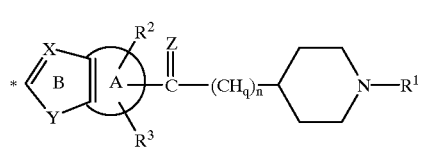

wherein one of R2 or R3 or the side chain containing —C(=Z)— may optionally be attached to the carbon atom designated by an asterisk in ring B;

ring A is benzo;

$R^1$ is phenyl, phenyl-$(C_1-C_6)$ alkyl, cinnamyl or heteroarylmethyl, wherein the heteroaryl moiety of said heteroarylmethyl is selected from imidazolo, thiazolo, thieno, pyrido and isoxazolo, and wherein said phenyl and said heteroaryl moiety may optionally be substituted with one or two substituents independently selected from $(C_1-C_6)$ alkyl, $(C_1-C_6)$alkoxy and halo;

$R^2$ and $R^3$ are independently selected from hydrogen, $(C_1-C_6)$alkoxy, $(C_1-C_6)$ alkyl optionally substituted with from one to three fluorine atoms, benzyloxy, hydroxy, phenyl, benzyl, halo, nitro, $COOR^4$, $CONHR^4$, $NR^4R^5$, $NR^4COR^5$, or $SO_pCH_2$— phenyl wherein p is 0, 1 or 2;

$R^4$ and $R^5$ are independently selected from hydrogen and $(C_1-C_6)$ alkyl, or $R^4$ and $R^5$, when part of said $NR^4R^5$, optionally form, together with the nitrogen to which they are attached, a ring containing four to eight members wherein one atom of the ring is nitrogen and the others are carbon, oxygen or nitrogen, or $R^4$ and $R^5$, when part of said $NR^4COR^5$, optionally form, together with the nitrogen and carbon to which they are attached, a four to eight membered lactam ring;

X is CH or $CCH_3$;

Y is S;

n is an integer from 1 to 4;

each q is independently 1 or 2; and

Z is oxygen or sulfur;

with the proviso that any $CH_q$ group wherein q is 1 must be attached to one and only one other $CH_q$ group wherein q is 1;

or a pharmaceutically acceptable salt of such compound.

10. A compound according to claim 9 having the formula

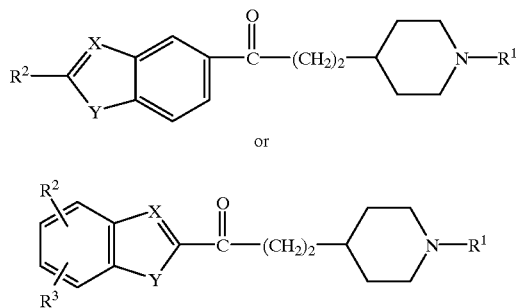

wherein $R^2$ and $R^3$ are independently selected from the group consisting of $(C_1-C_4)$alkyl, chloro, fluoro, methoxy, amino and —$NHC(=O)CH_3$; and $R^1$ is benzyl, methoxybenzyl, fluorobenzyl or a group of the formula

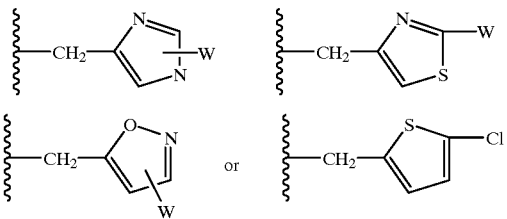

wherein W is hydrogen, $(C_1-C_6)$alkyl, phenyl or benzyl.

11. A compound according to claim 10 wherein $R^1$ is benzyl.

12. A compound according to claim 11 wherein $R^2$ and $R^3$ are independently selected from the group consisting of $(C_1-C_4)$alkyl, chloro, amino and —$NHC(=O)CH_3$.

13. A compound according to claim 10 selected from the group consisting of:

1-(5-methyl-benzo[b]thien-2-yl)-3-[1-(phenylmethyl)-4-piperidinyl]-1-propanone;

1-(6-methyl-benzo[b]thien-2-yl)-3-[1-(phenylmethyl)-4-piperidinyl)-1-propanone;

1-(3,5-dimethyl-benzo[b]thien-2-yl)-3-(1-(phenyl-methyl)-4-piperidinyl]-1-propanone; and 1-(benzo[b]thien-2-yl)-3-[1-(phenylmethyl)-4-piperidinyl]-1-propanone.

14. A pharmaceutical composition for enhancing memory or treating or preventing Alzheimer's disease comprising a compound according to claim 9 and a pharmaceutically acceptable carrier.

15. A pharmaceutical composition for inhibiting cholinesterase in a mammal comprising a compound according to claim 9 and a pharmaceutically acceptable carrier.

16. A method of inhibiting cholinesterase in a mammal comprising administering to said mammal a cholinesterase inhibiting amount of a compound according to claim 9.

17. A method of enhancing memory or treating or preventing Alzheimer's disease comprising administering to a patient a memory enhancing effective amount of a compound according to claim 9.

* * * * *